(12) United States Patent
Morishita et al.

(10) Patent No.: US 8,067,384 B2
(45) Date of Patent: Nov. 29, 2011

(54) CHIMERA (DOUBLE) DECOY

(75) Inventors: Ryuichi Morishita, Suita (JP); Toshio Ogihara, Minoh (JP); Motokuni Aoki, Kobe (JP); Takashi Miyake, Tamano (JP)

(73) Assignee: Anges MG, Inc., Osaka (JP)

( * ) Notice: Subject to any disclaimer, the term of this patent is extended or adjusted under 35 U.S.C. 154(b) by 1095 days.

(21) Appl. No.: 11/662,777

(22) PCT Filed: Oct. 20, 2005

(86) PCT No.: PCT/JP2005/019742
§ 371 (c)(1),
(2), (4) Date: Mar. 14, 2007

(87) PCT Pub. No.: WO2006/043722
PCT Pub. Date: Apr. 27, 2006

(65) Prior Publication Data
US 2007/0259826 A1 Nov. 8, 2007

(30) Foreign Application Priority Data
Oct. 22, 2004 (JP) ................................. 2004-308952

(51) Int. Cl.
C12N 15/11 (2006.01)
C12N 15/113 (2006.01)
C12N 15/115 (2006.01)
(52) U.S. Cl. ........ 514/44; 536/23.1; 536/24.1; 536/24.5
(58) Field of Classification Search .................... None
See application file for complete search history.

(56) References Cited

U.S. PATENT DOCUMENTS

| | | | |
|---|---|---|---|
| 6,034,234 A | 3/2000 | Matsuo et al. | |
| 6,262,033 B1 | 7/2001 | Morishita et al. | |
| 6,774,118 B1 | 8/2004 | Dzau et al. | |
| 6,821,956 B2 | 11/2004 | Dzau et al. | |
| 6,841,539 B1 | 1/2005 | Mehta et al. | |
| 7,060,690 B2 | 6/2006 | Klem et al. | |
| 7,482,158 B2 * | 1/2009 | Mathison | 435/375 |
| 2002/0052333 A1 | 5/2002 | Dzau et al. | |
| 2002/0098162 A1 | 7/2002 | Morishita et al. | |
| 2002/0128217 A1 | 9/2002 | Dzau et al. | |
| 2003/0176376 A1 | 9/2003 | Klem | |
| 2003/0186922 A1 | 10/2003 | Dzau et al. | |
| 2004/0072726 A1 | 4/2004 | Morishita et al. | |
| 2004/0109843 A1 | 6/2004 | Morishita et al. | |
| 2004/0162250 A1 | 8/2004 | Morishita et al. | |
| 2004/0162251 A1 | 8/2004 | Morishita et al. | |
| 2004/0229833 A1 | 11/2004 | Dzau et al. | |
| 2005/0096287 A1 | 5/2005 | Mehta et al. | |
| 2005/0175539 A1 | 8/2005 | Morishita et al. | |
| 2006/0116344 A1 | 6/2006 | Morishita et al. | |
| 2006/0135449 A1 | 6/2006 | Sawa et al. | |
| 2006/0241066 A1 | 10/2006 | Tomita et al. | |
| 2006/0263422 A1 | 11/2006 | Morishita et al. | |
| 2007/0014840 A1 | 1/2007 | Lee et al. | |
| 2008/0207552 A1 | 8/2008 | Sawa et al. | |
| 2009/0105183 A1 | 4/2009 | Morishita et al. | |

FOREIGN PATENT DOCUMENTS

| | | |
|---|---|---|
| JP | 2002-193813 | 7/2002 |
| JP | 3392143 | 1/2003 |
| WO | 95/11687 | 5/1995 |
| WO | 96/16074 | 5/1996 |
| WO | 96/35430 | 11/1996 |
| WO | 99/60167 | 11/1999 |

OTHER PUBLICATIONS

Nakashima et al., *Inhibition of Experimental Abdominal Aortic Aneurysm in the Rat by Use of Decoy Oligodeoxynucleotides Suppressing Activity of Nuclear Factor κB and ets Transcription Factors*, Circulation, Jan. 6, 2004, vol. 109, No. 1, pp. 132-138.

* cited by examiner

*Primary Examiner* — Maria Marvich
(74) *Attorney, Agent, or Firm* — Nixon & Vanderhye P.C.

(57) ABSTRACT

The present invention provides a prophylactic, ameliorative or therapeutic medicament for vascular restenosis, ischemic disease, allergic disease, inflammatory disease, autoimmune disease, or cancer metastasis, invasion (cancer metastasis/invasion) or cachexia based on the inhibitory action on a plural of transcriptional regulatory factor. A chimera (double) decoy of the present invention has plural transcriptional regulatory factor binding sequences in a single molecule thereof. Thus, it is able to inhibit the activity of plural transcriptional regulatory factors with a single molecule. For example, stenosis of an anastomosed site of an artificial blood vessel is caused by thickening of the vascular intima, and this is mainly caused by activation of cell proliferation by an inflammatory reaction occurring at the anastomosed site. Thus, thickening of vessel walls can be inhibited by simultaneously inhibiting two transcriptional regulatory factors involved in inflammation and cell proliferation by using the chimera decoy of the present invention.

1 Claim, 12 Drawing Sheets

Fig. 3
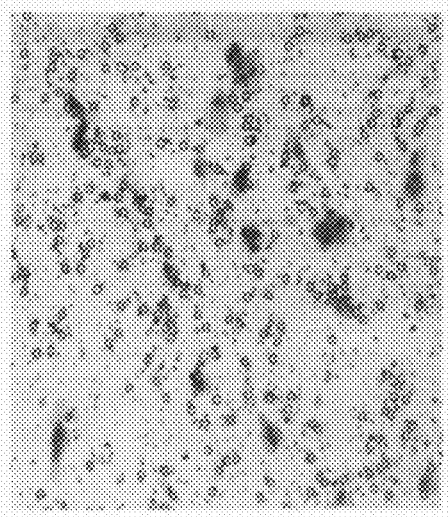
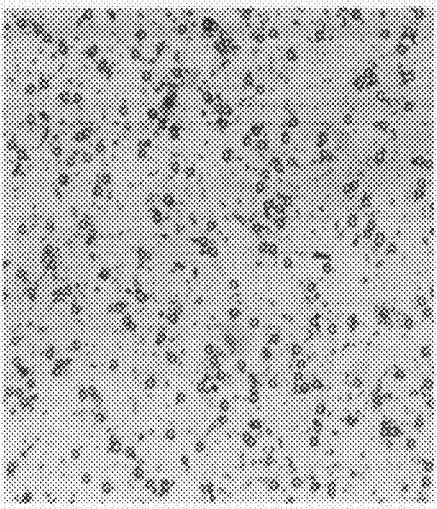
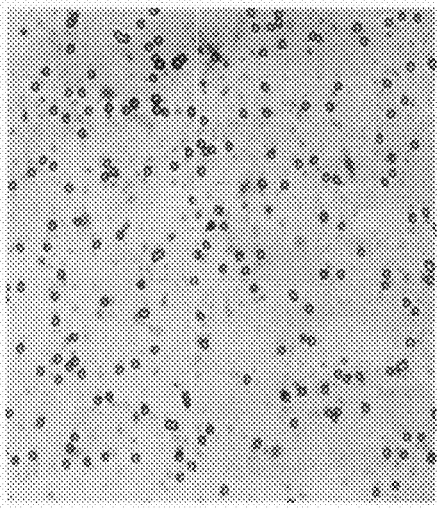
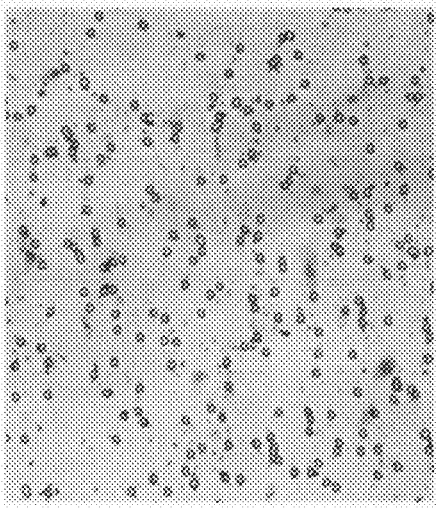
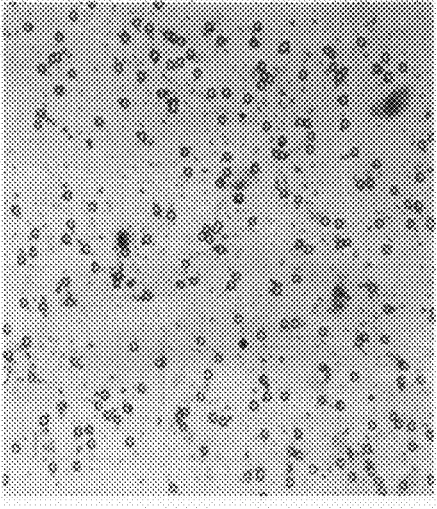

Fig. 6
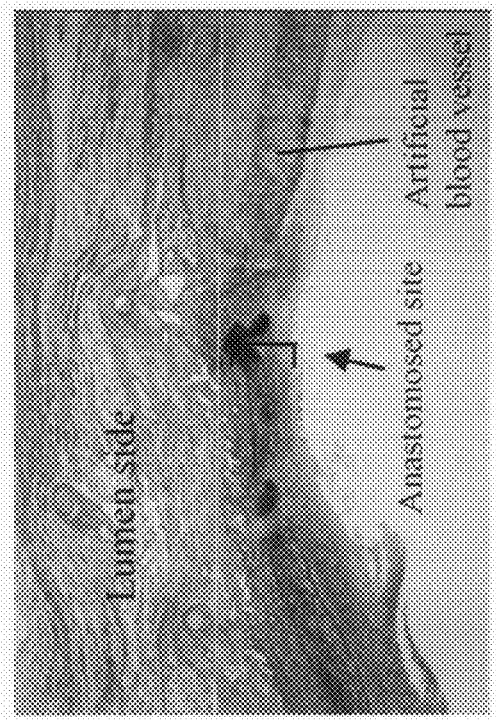
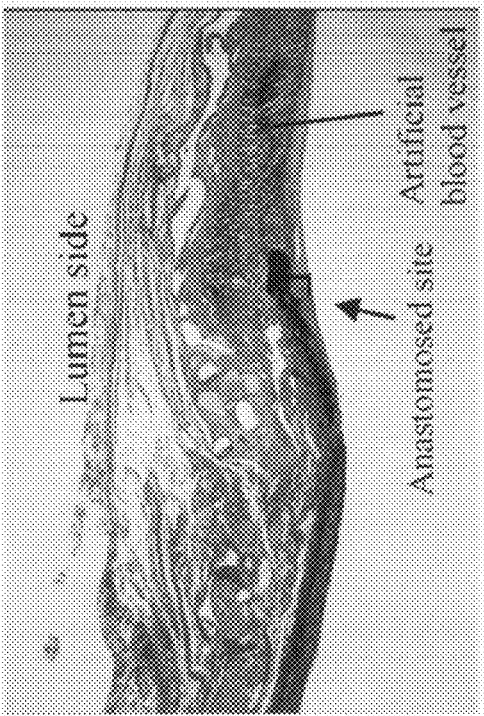
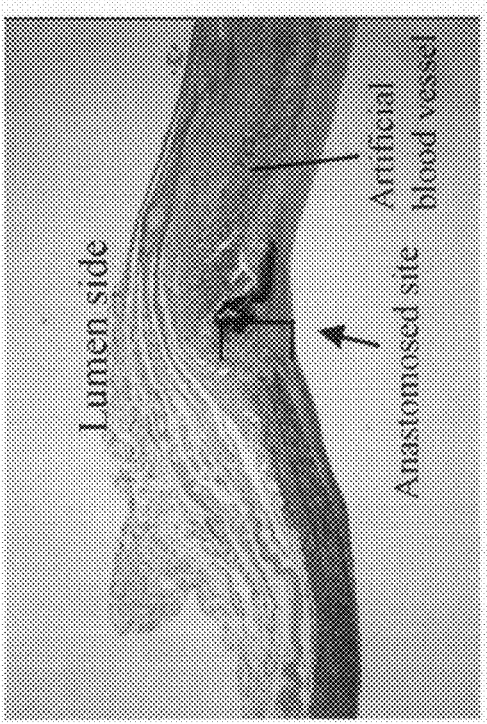

Fig. 9
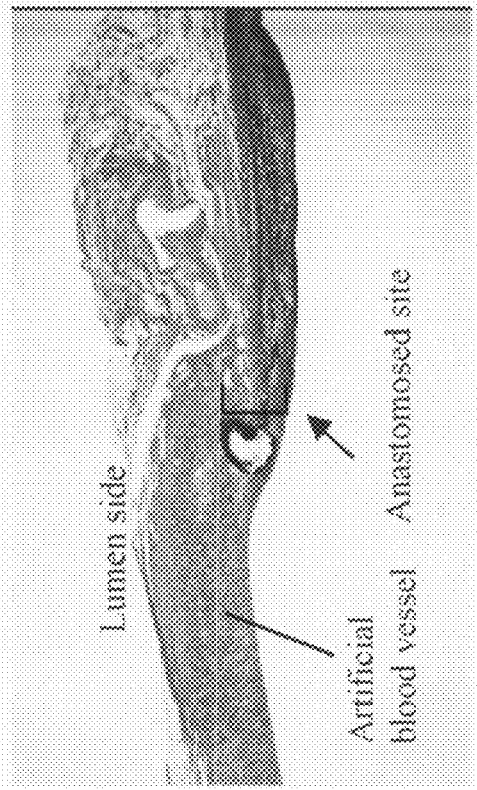
Control
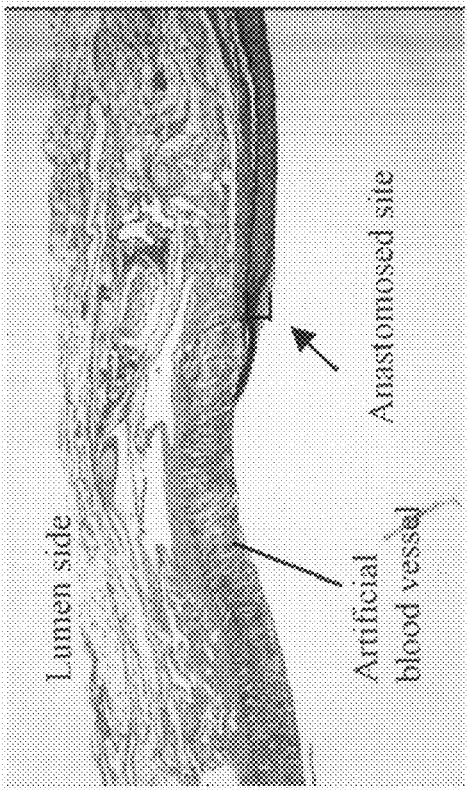
Chimera decoy
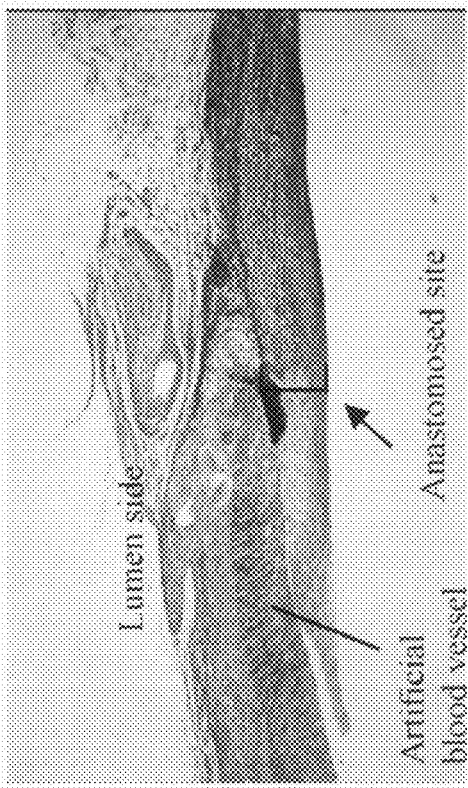
Scrambled decoy

Fig. 13
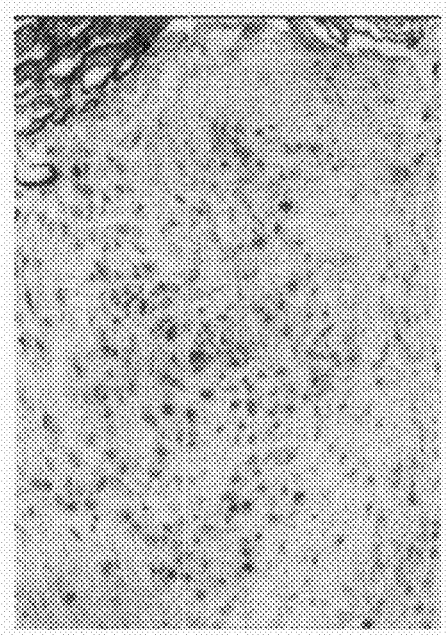
Scrambled decoy
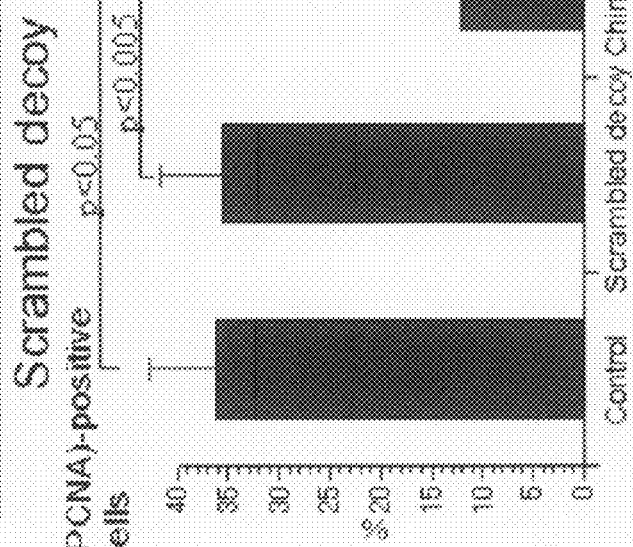
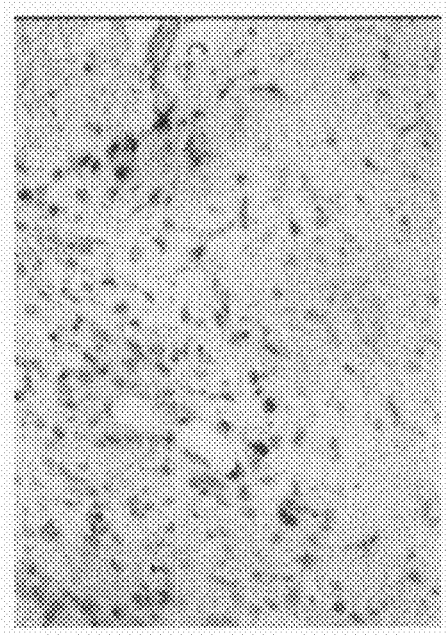
Control
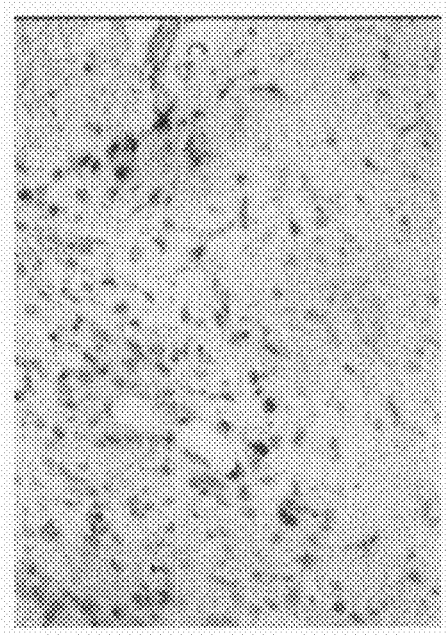
Chimera decoy

CHIMERA (DOUBLE) DECOY

This application is a U.S. national stage of International Patent Application No. PCT/JP2005/019742, filed 20 Oct. 2005, which designated the U.S. and claims priority of JP 2004-308952, filed 22 Oct. 2004; the entire contents of each of which are hereby incorporated by reference.

TECHNICAL FIELD

The present invention relates to a decoy comprising an oligonucleotide having a plural sequence bound by transcriptional regulatory factors, and a usage method thereof. More particularly, the present invention relates to a chimera (double) decoy oligonucleotide and a usage method thereof.

BACKGROUND ART

Artificial blood vessels are frequently used in surgical vascular reconstruction for treatment of diseases such as arteriosclerosis obliterans, aortic aneurysm and aortic dissection. In addition, balloon catheters and stents are frequently used to dilate occluded blood vessels. However, vessels frequently become reoccluded following surgery using these devices, thereby resulting in the problem of having to repeat the same procedure.

For example, although surgical vascular reconstruction is used to avoid amputation of a lower limb for patients with arteriosclerosis obliterans, bypass surgery using an artificial blood vessel is the first choice of treatment for lesions above the knee. However, occlusion of the artificial vessel may occur later than one month after surgery. This occlusion is mainly caused by thickening of the vascular intima at the anastomosed site. Inhibiting this thickening would make it possible to conserve grafts for a long period of time as well as to use artificial blood vessels for vascular reconstruction at locations below the knee.

The major cause of thickening of vascular intima at anastomosed sites of artificial blood vessels is the activation of cell proliferation by an inflammatory reaction occurring at the anastomosed site. Thus, inhibition of this cell proliferation is thought to be able to inhibit thickening.

Gene therapy techniques have been developed in recent years for the purpose of inhibiting inflammatory reactions. Research has been conducted which is expected to demonstrate anti-inflammatory effects by inhibiting the function of NF-κB, a transcriptional regulatory factor involved in inflammatory reactions, with a decoy nucleic acid.

International Patent Publication No. (WO-A1) 96/035430 discloses that an NF-κB decoy nucleic acid can be a therapeutic agent for inflammatory diseases.

In addition, gene therapy techniques for controlling cell proliferation have also been developed. For example, the proliferation of vascular media can be inhibited by inhibiting the function of E2F, a transcriptional regulatory factor that plays an important role in cell proliferation, with a decoy nucleic acid.

JP-B 3392143 discloses an anticancer agent with the use of an E2F decoy nucleic acid.

WO 95/11687 discloses that cell proliferation can be inhibited by using an E2F decoy nucleic acid.

Previously disclosed examples of oligonucleotides having two different functions within a single molecule are indicated below.

JP-A(W) 2002-515514 discloses a method for using an ICAM-1 antisense as an external skin medication, and although it is stated that it may have a DNA: RNA or RNA: DNA chimeric structure, there are no specific examples of chimera decoys indicated, including cited references. In addition, this publication discloses an invention relating to transdermal delivery of an antisense strand.

US-A 2003-176376 discloses that a hybrid molecule of a bcl-2 antisense and CRE decoy has the potential for treating diseases caused by abnormal cell growth such as cancer.

JP-A 2002-193813 indicates that a chimera decoy of NF-κB and Ets inhibits increase of aorta surface area in an aortic aneurysm model.

DISCLOSURE OF THE INVENTION

It is necessary to simultaneously inhibit inflammation and cell proliferation in order to more effectively prevent vascular restenosis. Thus, there is a need to develop a medicament inhibiting both of them in the proper balance, while also having superior pharmacological effects and safety.

JP-A(W) 2002-515514 does not describe any specific therapeutic effects, and the potential for application to various diseases is completely unknown.

US-A 2003-176376 does not mention the usefulness for diseases other than those listed above.

In the case of JP-A 2002-193813, usefulness for diseases other than those listed above is unknown.

An object of the present invention is to provide a medicament that has a decoy nucleic acid as an active ingredient and simultaneously inhibits inflammation and cell proliferation.

The inventors of the present invention thought that, since thickening of vascular intima at anastomosed sites is caused by invasion of inflammatory cells and proliferation and migration of smooth muscle cells due to inflammation of vessel walls, the development of a medicament capable of simultaneously controlling these with a single molecule would be effective.

As a result of extensive studies, the inventors of the present invention designed a molecule capable of simultaneously inhibiting, for example, inflammatory action controlled by NF-κB and cell proliferation action controlled by E2F. Namely, the inventors of the present invention found that a decoy having both the DNA binding sequences of NF-κB and E2F in a single molecule (chimera ((double) decoy) more effectively inhibits both transcriptional regulatory factors. A decoy refers to a double-strand oligonucleotide having a nucleic acid sequence bound by a transcriptional regulatory factor, and thereby acts as a decoy by competing with other nucleic acid sequences bound by said transcriptional regulatory factor. Although a decoy may be DNA or RNA, DNA is preferable. In addition, in the present description, decoy, decoy oligonucleotide and decoy ODN are used synonymously.

The gist of the present invention relates to:
(1) a chimera (double) decoy containing a plural transcriptional regulatory factor binding sequences in a single molecule;
(2) the decoy described in (1), wherein the chimera decoy is comprised of a DNA or RNA oligonucleotide;
(3) the decoy described in (1) or (2), wherein the chimera decoy is comprised of a DNA oligonucleotide;
(4) the decoy described in (1) to (3), wherein the chimera decoy has transcriptional regulatory factor inhibitory action;
(5) the decoy described in (1) to (4), wherein at least one transcriptional regulatory factor binding sequence of the chimera decoy is a sequence that binds NF-κB, E2F, GATA-3, STAT-1, STAT-6, Ets or AP-1;

(6) the decoy described in any of (1) to (5), wherein an NF-κB binding sequence in the chimera decoy is GGGRHTYYHC (SEQ ID NO:2; wherein, R represents A or G, Y represents C or T and H represents A, C or T);
(7) the decoy described in (6), wherein an NF-κB binding sequence in the chimera decoy is GGGATTTCCC (SEQ ID NO:9) or GGGACTTTCC (SEQ ID NO:10);
(8) the decoy described in any of (1) to (5), wherein an E2F binding sequence in the chimera decoy is TTTSSCGS (SEQ ID NO:3; wherein, S represents G or C);
(9) the decoy described in (8), wherein an E2F binding sequence in the chimera decoy is TTTCCCGC (SEQ ID NO:11);
(10) the decoy described in any of (1) to (5), wherein a GATA-3 binding sequence in the chimera decoy is WGATAR (SEQ ID NO:4; wherein, W represents A or T, and R represents A or G);
(11) the decoy described in (10), wherein a GATA-3 binding sequence in the chimera decoy is AGATAG (SEQ ID NO:12);
(12) the decoy described in any of (1) to (5), wherein an STAT-1 binding sequence in the chimera decoy is TTCNNNGAA (SEQ ID NO:5; wherein, N represents A, G, T or C);
(13) the decoy described in (12), wherein an STAT-1 binding sequence in the chimera decoy is TTCCGGGAA (SEQ ID NO:13);
(14) the decoy described in any of (1) to (5), wherein an STAT-6 binding sequence in the chimera decoy is TTCNNNNGAA (SEQ ID NO:6; wherein, N represents A, G, T or C);
(15) the decoy described in (14), wherein an STAT-6 binding sequence in the chimera decoy is TTCCCAAGAA (SEQ ID NO:14);
(16) the decoy described in any of (1) to (5), wherein an Ets binding sequence in the chimera decoy is MGGAW (SEQ ID NO:7; wherein, M represents A or C, and W represents A or T);
(17) the decoy described in (16), wherein an Ets binding sequence in the chimera decoy is CGGAA (SEQ ID NO:15);
(18) the decoy described in any of (1) to (5), wherein an AP-1 binding sequence in the chimera decoy is TGASTMA (SEQ ID NO:8; wherein, S represents G or C, and M represents A or C);
(19) the decoy described in (18), wherein an AP-1 binding sequence in the chimera decoy is TGAGTCA (SEQ ID NO:16);
(20) the decoy described in any of (1) to (19), wherein the chimera decoy contains two transcriptional regulatory factor binding sequences in a single molecule thereof;
(21) the decoy described in any of (1) to (20), wherein the chimera decoy is comprised of an oligonucleotide indicated in the following formula:
5'-N(m)-Consensus 1-N(s)-Consensus 2-N(n)-3' (wherein, N(m) represents a 5'-terminal flanking sequence, N(s) represents a spacer, and N(n) represents a 3'-terminal flanking sequence; Consensus 1 and Consensus 2 represent transcriptional regulatory factor binding sequences; m, s and n respectively and independently represent 0 or an integer of 1 to 20; and N represents a nucleotide A, G, T or C);
(22) the decoy described in any of (1) to (21), wherein Consensus 1 and/or Consensus 2 are sequences selected from the group consisting of GGGRHTYYHC (SEQ ID NO:2; wherein, R represents A or G, Y represents C or T, and H represents A, C or T), TTTSSCGS (SEQ ID NO:3; wherein, S represents G or C), WGATAR (SEQ ID NO:4; wherein, W represents A or T, and R represents A or G), TTCNNNGAA (SEQ ID NO:5; wherein, N represents A, G, T or C), TTCNNNNGAA (SEQ ID NO:6; wherein, N represents A, G, T or C), MGGAW (SEQ ID NO:7; wherein, M represents A or C, and W represents A or T) and TGASTMA (SEQ ID NO:8; wherein, S represents G or C, and M represents A or C);
(23) the decoy described in any of (1) to (22), wherein Consensus 1 and/or Consensus 2 are sequences selected from the group consisting of GGGATTTCCC (SEQ ID NO:9), GGGACTTTCC (SEQ ID NO:10), TTTCCCGC (SEQ ID NO:11), AGATAG (SEQ ID NO:12), TTCCGGGAA (SEQ ID NO:13), TTCCCAAGAA (SEQ ID NO:14), CGGAA (SEQ ID NO:15) and TGAGTCA (SEQ ID NO:16);
(24) the decoy described in any of (21) to (23), wherein (m) is 0 or an integer of 1 to 20 in the formula of (21);
(25) the decoy described in any of (21) to (24), wherein (m) is 0 or an integer of 1 to 10 in the formula of (21);
(26) the decoy described in any of (21) to (25), wherein (m) is 0 or an integer of 1 to 5 in the formula of (21);
(27) the decoy described in any of (21) to (26), wherein (s) is 0 or an integer of 1 to 20 in the formula of (21);
(28) the decoy described in any of (21) to (27), wherein (s) is 0 or an integer of 1 to 10 in the formula of (21);
(29) the decoy described in any of (21) to (28), wherein (s) is 0 or an integer of 1 to 5 in the formula of (21);
(30) the decoy described in any of (21) to (29), wherein (n) is 0 or an integer of 1 to 20 in the formula of (21);
(31) the decoy described in any of (21) to (30), wherein (n) is 0 or an integer of 1 to 10 in the formula of (21);
(32) the decoy described in any of (21) to (31), wherein (n) is 0 or an integer of 1 to 5 in the formula of (21);
(33) the decoy described in any of (1) to (32), wherein the chimera decoy is a chimera decoy of NF-κB and another transcriptional regulatory factor;
(34) the decoy described in any of (1) to (33), wherein the chimera decoy is a chimera decoy of NF-κB and E2F;
(35) the decoy described in any of (1) to (34), wherein the chimera decoy is the chimera decoy represented by Sequence No. 1;
(36) the decoy described in any of (1) to (35), wherein the chimera decoy is composed of double-strand DNA;
(37) a pharmaceutical composition containing the decoy described in any of (1) to (36);
(38) a prophylactic, ameliorative or therapeutic medicament for an ischemic disease, allergic disease, inflammatory disease, autoimmune disease, or cancer metastasis, invasion (cancer metastasis/invasion) or cachexia, comprising the decoy described in any of (1) to (37);
(39) a prophylactic, ameliorative or therapeutic medicament for vascular restenosis, acute coronary syndrome, cerebral ischemia, myocardial infarction, reperfusion injury of ischemic diseases, atopic dermatitis, psoriasis vulgaris, contact dermatitis, kelloids, bedsores, ulcerative colitis, Crohn's disease, nephropathia, glomerular sclerosis, albuminuria, nephritis, renal insufficiency, chronic rheumatoid arthritis, osteoarthritis, asthma or chronic obstructive pulmonary disease (COPD), comprising the decoy described in any of (1) to (37);
(40) a prophylactic, ameliorative or therapeutic medicament for vascular restenosis following percutaneous transluminal coronary angioplasty (PTCA), percutaneous transluminal angioplasty (PTA), bypass surgery, organ transplant or organ surgery, comprising the decoy described in any of (1) to (37);

(41) the prophylactic, ameliorative or therapeutic medicament comprising the decoy described in any of (1) to (37), wherein the vascular restenosis is restenosis caused by the use of an artificial blood vessel, catheter or stent or by vein transplant;
(42) the prophylactic, ameliorative or therapeutic medicament comprising the decoy described in any of (1) to (37), wherein the vascular restenosis is caused by surgical treatment for arteriosclerosis obliterans, aneurysm, aortic dissection, acute coronary syndrome, cerebral ischemia, marfan syndrome or plaque rupture;
(43) use of the decoy described in any of (1) to (37) for producing a prophylactic, ameliorative or therapeutic medicament for an ischemic disease, allergic disease, inflammatory disease, autoimmune disease, or cancer metastasis, invasion (cancer metastasis/invasion) or cachexia; and
(44) a method for prophylaxis, amelioration or treatment for an ischemic disease, allergic disease, inflammatory disease, autoimmune disease, or cancer metastasis, invasion (cancer metastasis/invasion) or cachexia, which comprises using the decoy according to any of claims 1 to 37.

A chimera decoy of the present invention is a nucleic acid-based medicament that simultaneously inhibits a plural transcriptional regulatory factors as a single molecule. This chimera decoy can be used for, for example, an ischemic disease, allergic disease, inflammatory disease, autoimmune disease, or cancer metastasis, invasion (cancer metastasis/invasion) or cachexia. More preferably, this chimera decoy can be used for restenosis following percutaneous transluminal coronary angioplasty (PTCA), percutaneous transluminal angioplasty (PTA) or bypass surgery used for the surgical treatment of arteriosclerosis obliterans, aneurysm, aortic dissection, marfan syndrome or plaque rupture.

DETAILED DESCRIPTION OF THE INVENTION

The present invention provides a decoy nucleic acid (chimera (double) decoy) having plural transcriptional regulatory factor binding sequences as a single molecule thereof, and a pharmaceutical composition having this decoy nucleic acid as an active ingredient thereof.

In the present description, a chimera decoy refers to a decoy having two or more transcriptional regulatory factor binding sequences, while a double decoy refers to a decoy having two transcriptional regulatory factor binding sequences. Thus, a double decoy is included in the concept of a chimera decoy.

Although examples of decoys of the present invention include decoys of NF-κB, STAT-1, GATA-3, STAT-6, AP-1, Ets and E2F, a chimera decoy combining, for example, NF-κB and E2F is preferable. A combined chimera decoy can be produced by selecting the NF-κB binding sequence from the consensus sequence GGGRHTYYHC (R(A,G); Y(C,T); H(A,C,T)) (SEQ ID NO:2), and selecting the E2F binding sequence from the consensus sequence TTTSSCGS (S(G,C)) (SEQ ID NO:3). For example, preferable examples of a chimera decoy include, but are not limited to, GAAGGATTTCCCTCCATTTCCCGCGGA (SEQ ID NO:1) (chimera decoy of NF-κB and E2F) having for core sequences thereof GGGATTTCCC (SEQ ID NO:9) of NF-κB and TTTCCCGC (SEQ ID NO:11) of E2F.

In addition, sequences selected from the GATA-3 consensus sequence WGATAR (W(A,T); R(A,G)) (SEQ ID NO:4), the STAT-1 consensus sequence TTCNNNGAA (N(A,G,T,C)) (SEQ ID NO:5), the STAT-6 consensus sequence TTCNNNNGAA (N(A,G,T,C)) (SEQ ID NO:6), the Ets consensus sequence MGGAW (M(A,C); W(A,T)) (SEQ ID NO:7), and the AP-1 consensus sequence TGASTMA (S(G,C); M(A,C)) (SEQ ID NO:8) can also be used in a suitable combination thereof. Examples of such combinations include, but are not limited to, suitable combinations of NF-κB binding sequence GGGACTTTCC (SEQ ID NO:10), GATA-3 binding sequence AGATAG (SEQ ID NO:12), STAT-1 binding sequence TTCCGGGAA (SEQ ID NO:13), STAT-6 binding sequence TTCCCAAGAA (SEQ ID NO:14), Ets binding sequence CGGAA (SEQ ID NO:15) and AP-1 binding sequence TGAGTCA (SEQ ID NO:16).

A chimera decoy as claimed in the present invention can be defined with the following formula:

$$5'\text{-N(m)-Consensus 1-N(s)-Consensus 2-N(n)-}3'$$

(wherein, N(m) represents a 5'-terminal flanking sequence, N(s) represents a spacer, and N(n) represents a 3'-terminal flanking sequence; Consensus 1 and Consensus 2 represent transcriptional regulatory factor binding sequences; m, s and n respectively and independently represent 0 or an integer of 1 to 20; and N represents a nucleotide A, G, T or C).

With respect to the 5'-terminal flanking sequence of the formula, although (m) is normally 0 or an integer of 1 to 20, (m) is preferably 0 or an integer of 1 to 10, and more preferably 0 or an integer of 1 to 5. In addition, although (s) of the spacer in the formula is normally 0 or an integer of 1 to 20, (s) is preferably 0 or an integer of 1 to 10, and more preferably 0 or an integer of 1 to 5. With respect to the 3'-terminal flanking sequence in the formula, although (n) is normally 0 or an integer of 1 to 20, (n) is preferably 0 or an integer of 1 to 10, and more preferably 0 or an integer of 1 to 5.

Although a DNA or RNA oligonucleotide is normally used for a chimera decoy of the present invention, double-strand DNA is preferable. In addition, oligonucleotides containing a complement thereto, mutants thereof, or compounds containing these in a molecule thereof can also be used. In addition, modified nucleic acids and/or pseudo nucleic acids may also be contained in these oligonucleotides. Examples of these nucleic acid-based medicaments include double-strand oligonucleotides or mutants thereof containing two or more of the above-mentioned nucleic acid sequences.

Furthermore, a chimera decoy as claimed in the present invention can be produced according to ordinary methods such as the use of a DNA synthesizer.

In addition, although varying according to age, body weight, symptoms, therapeutic effects, administration method and soon, the dose of a chimera decoy as claimed in the present invention is administered by introducing a decoy solution having a concentration of normally 0.1 to 1000 μmol/L, preferably 1 to 100 μmol/L and more preferably 10 to 80 μmol/L to a treatment site by, for example, cannulation. A chimera decoy as claimed in the present invention can be administered normally at 0.1 to 10,000 nmol, preferably 1 to 1,000 nmol and more preferably 10 to 100 nmol, as the daily adult dose using these solutions. A decoy nucleic acid solution is normally introduced at a pressure of 25 to 250 mmHg, preferably 50 to 200 mmHg, and more preferably 100 to 175 mmHg.

INDUSTRIAL APPLICABILITY

The present invention provides a prophylactic, ameliorative or therapeutic medicament for vascular restenosis, ischemic disease, allergic disease, inflammatory disease, cancer metastasis, invasion (cancer metastasis/invasion) or cachexia based on action that inhibits plural transcriptional regulatory factors.

BRIEF DESCRIPTION OF THE DRAWINGS

FIG. 3 shows micrographs of cells following a vascular smooth muscle cell migration assay (magnification: ×400).

FIG. 6 shows micrographs of distal anastomosed sites of rabbit blood vessels having undergone bypass surgery (magnification: ×100). The upward direction in the micrographs indicates the vascular lumen side, the anastomosis sites of artificial blood vessel are indicated by the arrows, and it is observed that chimera decoy inhibited thickening of the anastomosed site more than the control and the scrambled decoy.

FIG. 9 shows micrographs of proximal anastomosed sites of rabbit blood vessels having undergone bypass surgery (magnification: ×100) The upward direction in the micrographs indicates the vascular lumen side, the anastomosis sites of artificial blood vessel are indicated by the arrows, and it is observed that chimera decoy inhibited thickening of the anastomosed site more than the control and the scrambled decoy.

FIG. 13 shows micrographs of immunohistochemical staining of proliferating cell nuclear antigen (PCNA)—positive cells of graft anastomosed sites excised from a rabbit bypass model (magnification: ×400) and a graph showing the proportions of PCNA-positive cells among all cells.

EXAMPLES

Although the following indicates examples of the present invention to provide a detailed explanation thereof, the present invention is not limited to these examples.

1. Vascular Smooth Muscle Cell Proliferation Assay

Vascular smooth muscle cells having undergone 5 to 6 rounds of subculturing (VSMC, Sanko Junyaku, cryo AOSMC, Cat. No. CC-2571) were seeded onto a 96-well plate at $5 \times 10^3$ cells/well followed by culturing for 48 hours in serum-free medium. After introducing decoy ODN (20 nM or 600 nM) into the cells using Oligofectamine (Oligofectamine Reagent, Invitrogen, Cat. No. 12252-011), the cells were additionally cultured for 24 hours in serum-free medium. The sequence of the decoy ODN are shown below.

```
Chimera decoy      5'-GAAGGGATTTCC       (Sequence No. 1)
                   CTCCATTTCCCGCGG
                   A-3'
                   3'-CTTCCCTAAAGG
                   GAGGTAAAGGGCGCC
                   T-5'

Scrambled decoy    5'-CGTACCTGACTT       (Sequence No. 17)
                   AGCCATTTCGAGCGG
                   A-3'
                   3'-GCATGGACTGAA
                   TCGGTAAAGCTCGCC
                   T-5'

NF-κB decoy        5'-CCTTGAAGGGAT       (Sequence No. 18)
                   TTCCCTCC-3'
                   3'-GGAACTTCCCTA
                   AAGGGAGG-5'

E2F decoy          5'-CTAGATTTCCCG       (Sequence No. 19)
                   CG-3'
                   3'-TAAAGGGCGCCT       (Sequence No. 20)
                   AG-5'
```

After stimulating for 24 hours with platelet-derived growth factor (PGDF)-BB (10 ng/ml) (PeproTech EC Ltd., Cat. No. 100-14B), the medium was replaced with serum-free medium and 24 hours later, the number of cells were counted using a WST-1 cell counting kit (Cell Counting Kit, Dojindo Laboratories).

Figure 1:
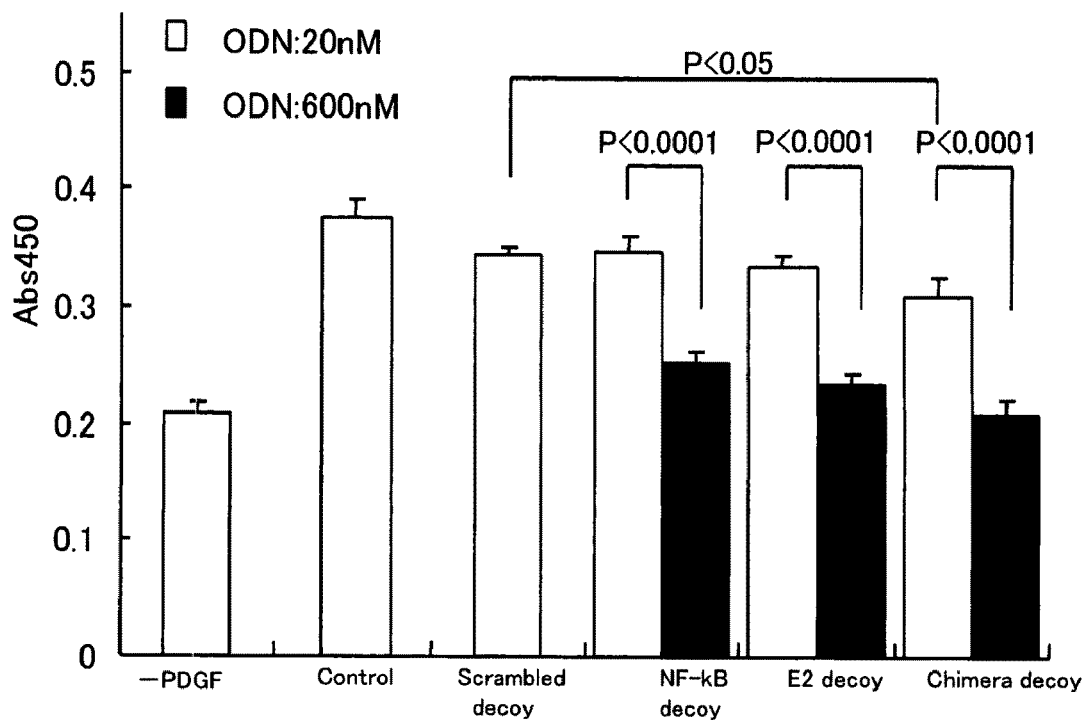
FIG. 1 is a graph showing the results of a vascular smooth muscle cell proliferation assay (wherein, "-PDGF" indicates normal (not stimulated with PDGF), hereinafter the same).

Results: The chimera decoy significantly inhibited vascular smooth muscle cell proliferation in comparison with the scrambled decoy (see Table 1, FIG. 1).

TABLE 1

| | (Abs450) | |
|---|---|---|
| | 20 nM ODN | 600 nM ODN |
| Normal (not stimulated with PDGF) | 0.21 ± 0.008 | |
| Control (stimulated with PDGF) | 0.38 ± 0.018 | |
| Scrambled decoy | 0.35 ± 0.007 | |
| Chimera decoy | 0.31 ± 0.015 | 0.208 ± 0.013 |
| NF-kB decoy | 0.35 ± 0.011 | 0.253 ± 0.009 |
| E2F decoy | 0.33 ± 0.011 | 0.233 ± 0.009 |

2. Vascular Endothelial Cell Proliferation Assay

Vascular endothelial cells having undergone 5 to 6 rounds of subculturing (EC, Sanko Junyaku, cryo HAEC, Cat. No. CC-2535) were seeded onto a 96-well plate at $1 \times 10^4$ cells/well followed by culturing for 48 hours in 0.5% serum medium. After introducing decoy ODN (600 nM) into the cells using Oligofectamine, the cells were additionally cultured for 24 hours in 0.5% serum medium. After stimulating for 24 hours with 5% serum medium, the medium was replaced with 0.5% serum medium and 24 hours later, the number of cells were counted using a WST-1 cell counting kit.

Figure 2:
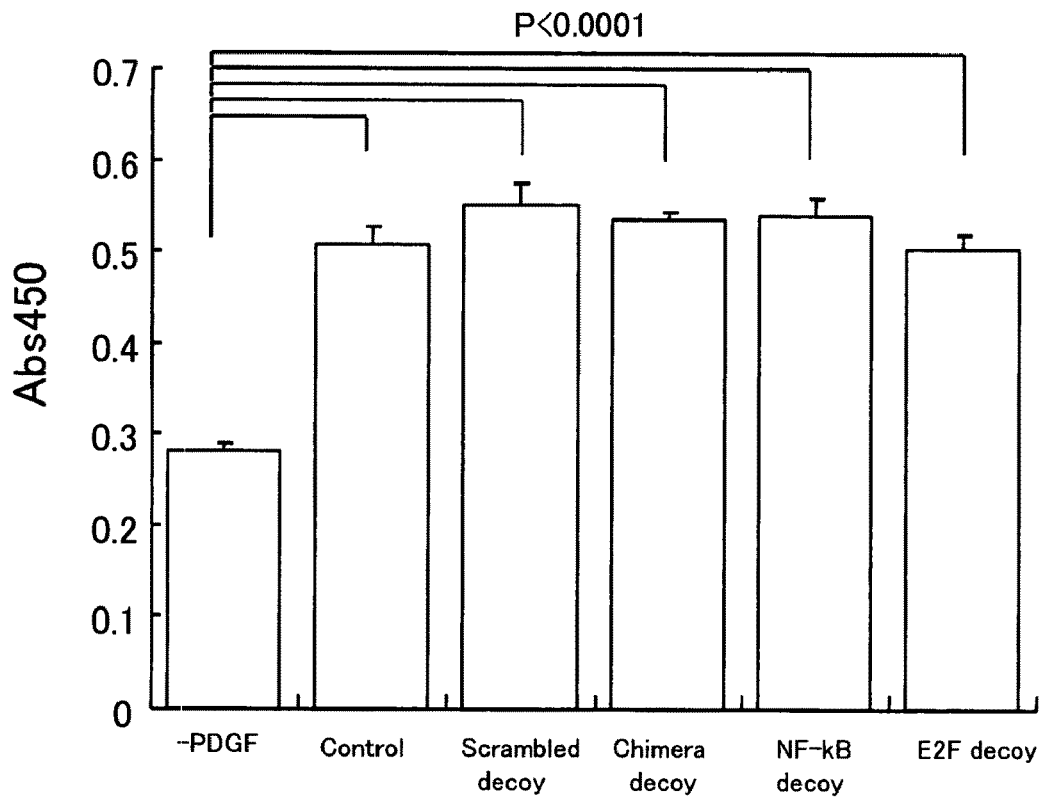
FIG. 2 is a graph showing the results of a vascular epithelial cell proliferation assay.

Results: None of the ODN, including the chimera decoy, inhibited proliferation of vascular endothelial cells (see Table 2, FIG. 2).

TABLE 2

| | (Abs450) |
|---|---|
| | 600 nM ODN |
| Normal (not stimulated with PDGF) | 0.28 ± 0.006 |
| Control (stimulated with PDGF) | 0.51 ± 0.016 |
| Scrambled decoy | 0.55 ± 0.022 |
| Chimera decoy | 0.54 ± 0.008 |
| NF-kB decoy | 0.54 ± 0.018 |
| E2F decoy | 0.51 ± 0.017 |

3. Vascular Smooth Muscle Cell Migration Assay

VSMC having undergone 5 to 6 rounds of subculturing were seeded onto a 6-well plate to 50% confluence followed by culturing for 48 hours in serum-free medium. After introducing decoy ODN (600 nM) into the cells using Oligofectamine, the cells were additionally cultured for 24 hours in serum-free medium. $2.5 \times 10^4$ of the VSMC were then seeded on the upper chamber of a 24-well Matrigel Invasion Chamber, and PDGF-BB (50 ng/ml) were added to the lower chamber to stimulate the cells for 48 hours. Subsequently, the number of migrating cells were then stained with Diff Quik stain and counted.

Figure 4:
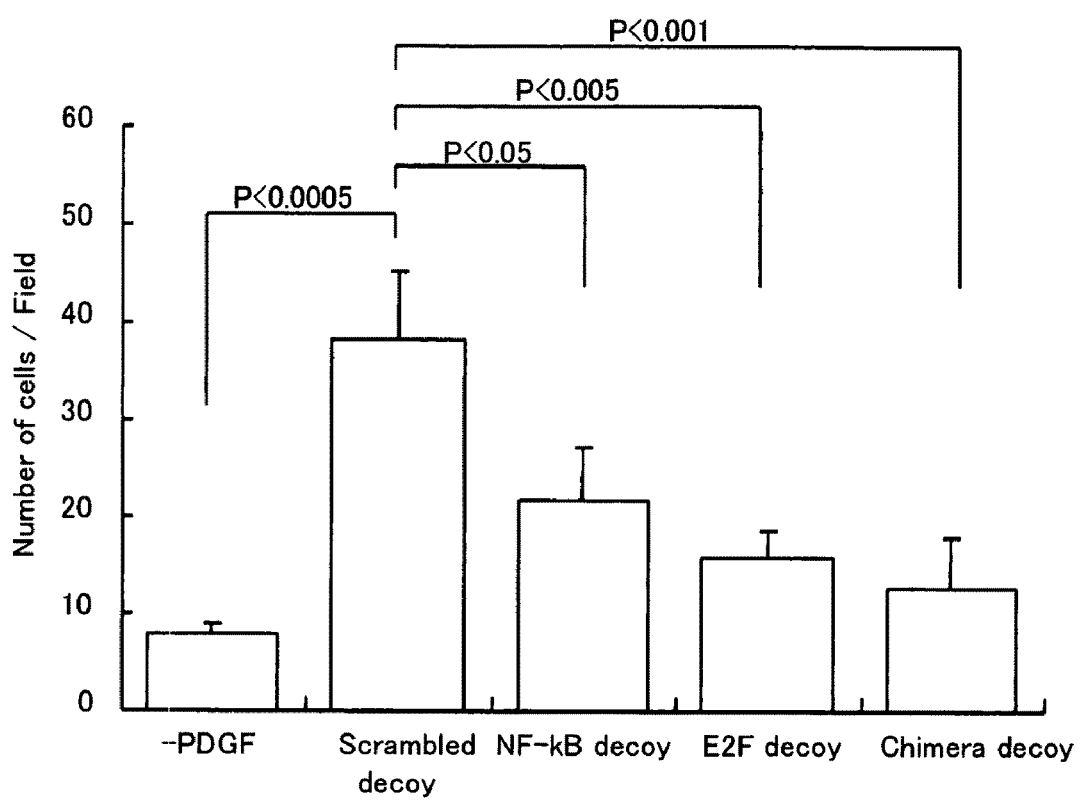
FIG. 4 is a graph showing the results of a vascular smooth muscle cell migration assay.

Results: The chimera decoy, the NF-κB decoy and the E2F decoy significantly inhibited cell migration as compared with the scrambled decoy, and the chimera decoy demonstrated the most potent activity (see Table 3, FIGS. 3 and 4).

TABLE 3

| (No. of cells/Field) | |
|---|---|
| | 600 nM ODN |
| Normal (not stimulated with PDGF) | 8 ± 1.1 |
| Scrambled decoy | 38.4 ± 6.9 |
| Chimera decoy | 12.8 ± 5.0 |
| NF-κB decoy | 21.8 ± 5.5 |
| E2F decoy | 15.8 ± 2.7 |

4. Rabbit Bypass Model Experiment

Figure 5:
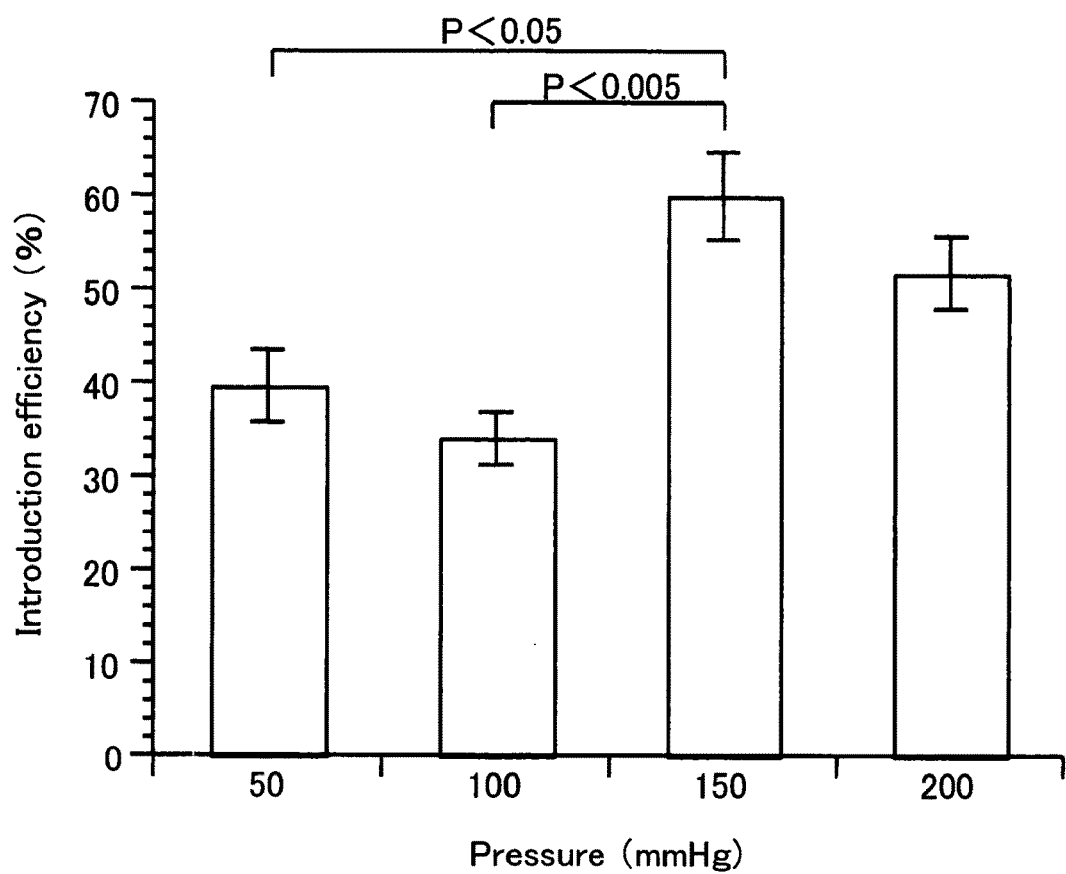
FIG. 5 is a graph comparing introduction rates of a decoy ODN to rabbit vascular wall.
Figure 7:
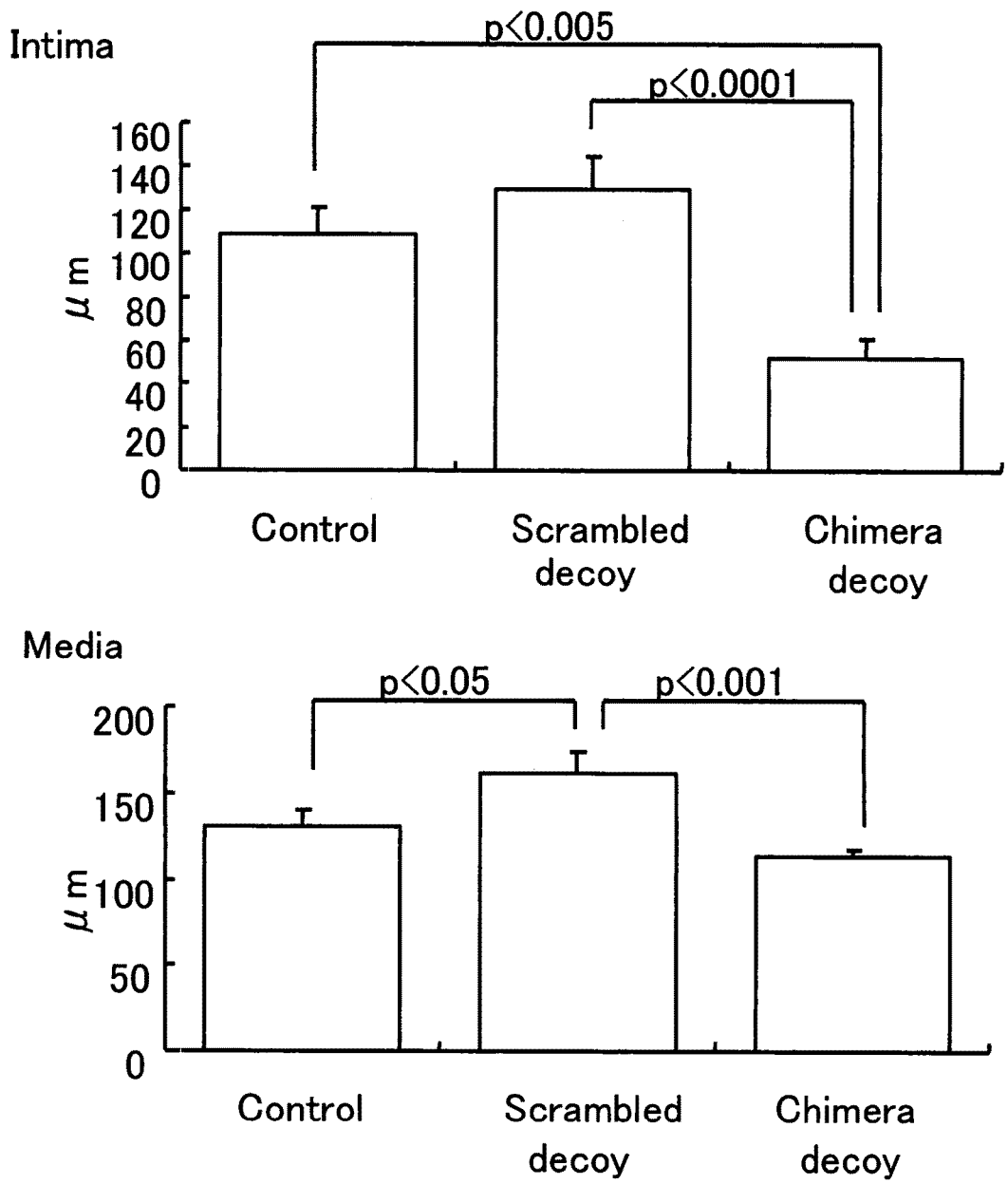
FIG. 7 are graphs showing the thicknesses of the intima and media of distal anastomosed sites of rabbit blood vessels having undergone bypass surgery.
Figure 8:
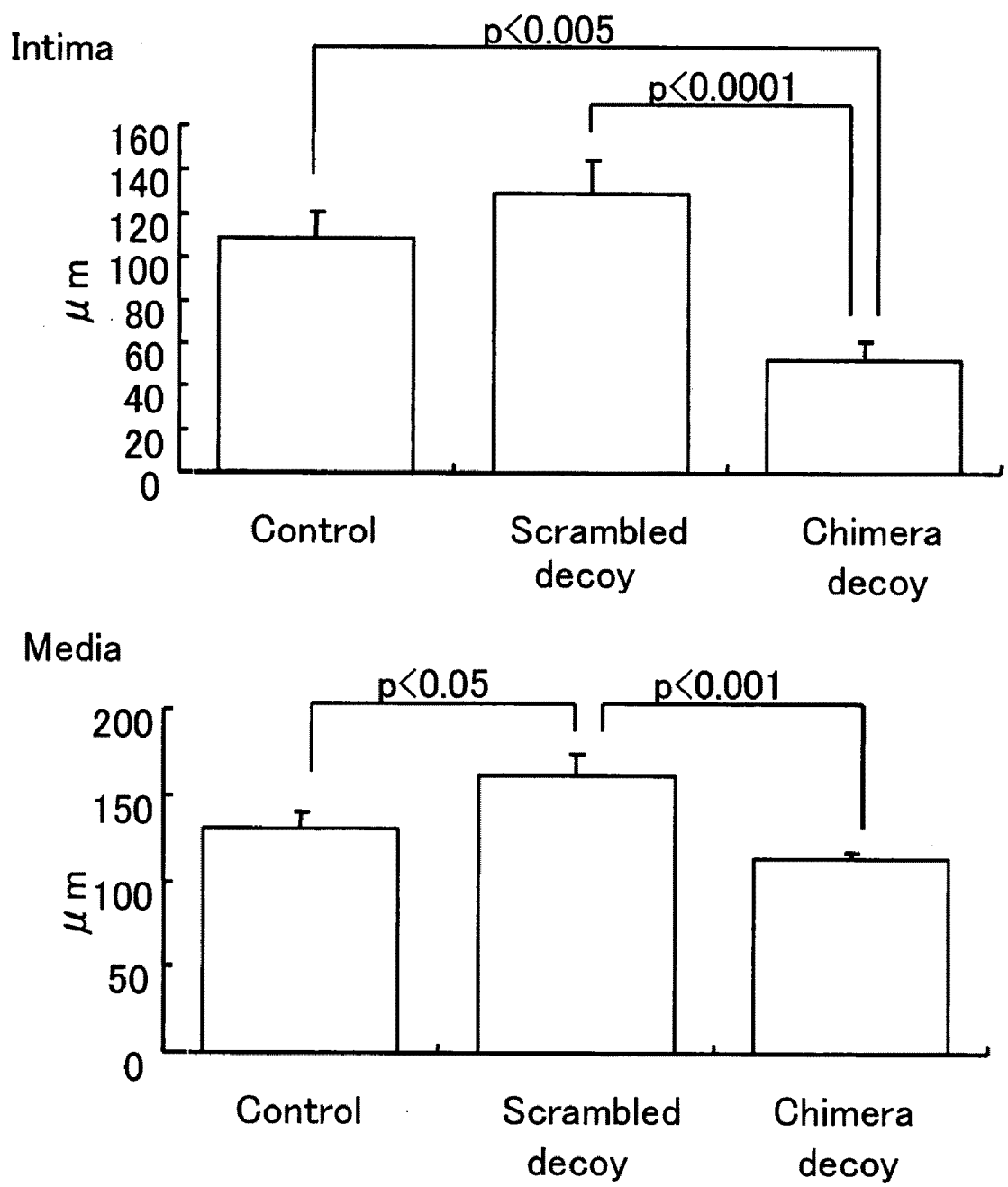
FIG. 8 is a graph showing a ratio of the thicknesses of the intima and media of anastomosed sites of rabbit blood vessels having undergone bypass surgery.
Figure 10:
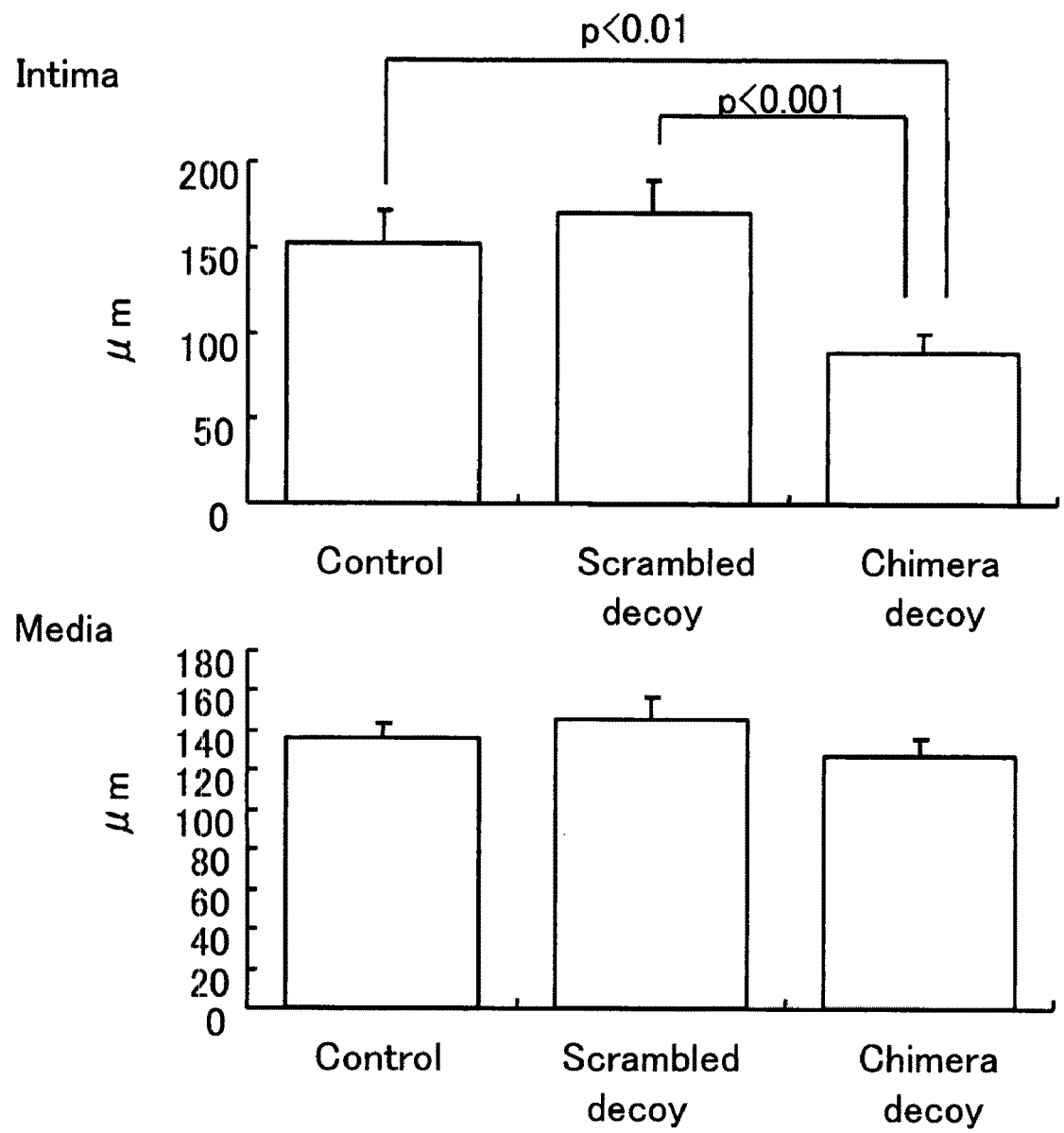
FIG. 10 are graphs showing the thicknesses of intima and media of proximal anastomosed sites of rabbit blood vessels having undergone bypass surgery.
Figure 11:
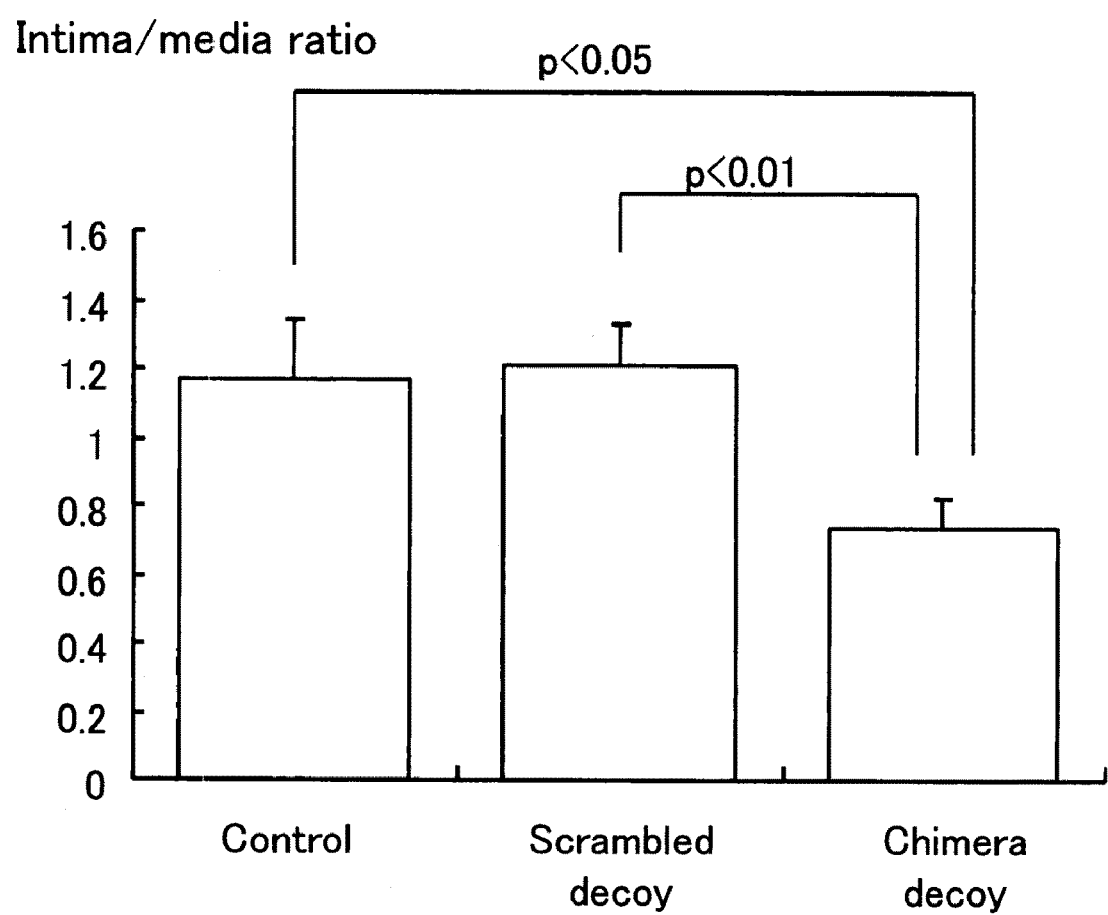
FIG. 11 is a graph showing the ratio of intima to media of proximal anastomosed sites of rabbit blood vessels having undergone bypass surgery.

The most suitable pressure for introducing decoy ODN into the artery wall was determined. FITC-ODN (40 µmol/L) was introduced at an arbitrary pressure into an artery anastomosed site. Measurement of the introduction efficiency clearly demonstrated the most suitable pressure to be 150 mmHg (see Table 4, FIG. 5).

TABLE 4

| Pressure (mmHg) | Introduction efficiency (%) |
|---|---|
| 50 | 39.6 ± 3.8 |
| 100 | 34.1 ± 2.8 |
| 150 | 60.0 ± 4.7 |
| 200 | 51.8 ± 3.9 |

After ablating the common carotid artery of hyperlipemic domestic rabbits and cannulating the artery, decoy ODN (40 µmol/L) introduced into the artery wall at a pressure of 150 mmHg. A 2 mm expanded polytetrafluoroethylene (ePTFE) graft (2 cm) was replaced at the introduction site to create a bypass model. Four weeks later, thickening of the intima at the anastomosed site was measured and evaluated by Elastica Van Gieson (EVG) staining.

Results: The chimera decoy significantly inhibited thickening of the intima and media at the anastomosed site as compared with the scrambled decoy. The chimera decoy demonstrated similar inhibitory activity regardless of the whether the anastomosed site was distal (location far from the body center) or proximal (location close to the body center) (see Tables 5 and 6, FIGS. 6 to 11).

TABLE 5

| Distal Anastomosed Site (µm) | | | |
|---|---|---|---|
| | Intima | Media | Intima/Media ratio |
| Control | 109.03 ± 11.87 | 130.38 ± 10.09 | 0.929 ± 0.125 |
| Scrambled decoy | 129.49 ± 15.51 | 161.79 ± 12.69 | 0.822 ± 0.081 |
| Chimera decoy | 52.63 ± 8.57 | 112.58 ± 5.10 | 0.447 ± 0.069 |

TABLE 6

| Proximal Anastomosed Site (µm) | | | |
|---|---|---|---|
| | Intima | Media | Intima/Media ratio |
| Control | 152.41 ± 10.06 | 136.66 ± 7.42 | 1.17 ± 0.17 |
| Scrambled decoy | 170.92 ± 17.64 | 146.26 ± 10.53 | 1.21 ± 0.12 |
| Chimera decoy | 89.50 ± 10.06 | 128.26 ± 7.49 | 0.73 ± 0.09 |

5. Macrophage and Proliferating Cell Nuclear Antigen (PCNA) Staining

The proportions of macrophages and PCNA among cells at the graft anastomosed site excised from the rabbit bypass model used in 4 above were investigated. Immunohistochemical staining was carried out using peroxidase and an avidin-biotin complex system.

The paraffin from paraffin sections having a thickness of 5 µm was removed followed by rehydration. Endogenous peroxidase was blocked by using 3% hydrogen peroxide. Blocking was carried out for 30 minutes using phosphate-buffered saline (PBS) containing 5% horse serum. Primary antibody diluted by 1:50 was added to the sections followed by incubating overnight at 4° C. RAM11 antibody (Dako, USA) was used to detect macrophages, while PCNA antibody (Clone: PC10) (Dako, USA) was used to detect PCNA. PBS containing biotinated anti-mouse IgG (Vector Laboratories, Burlingame, Calif., USA) was added to the sections followed by incubation for 30 minutes while being suitably washed with PBS. Then, PBS containing avidin-biotinated horseradish peroxidase was added followed by further incubation for 30 minutes. This was carried out using the Vectastain Elite ABC Kit (Vector Laboratories) according to the instructions provided with the kit. Immune complex was detected using 0.05% 3,3'-diaminobenzidine (DAB, Vector Laboratories), after which the sections were counter-stained with hematoxylin.

Figure 12:
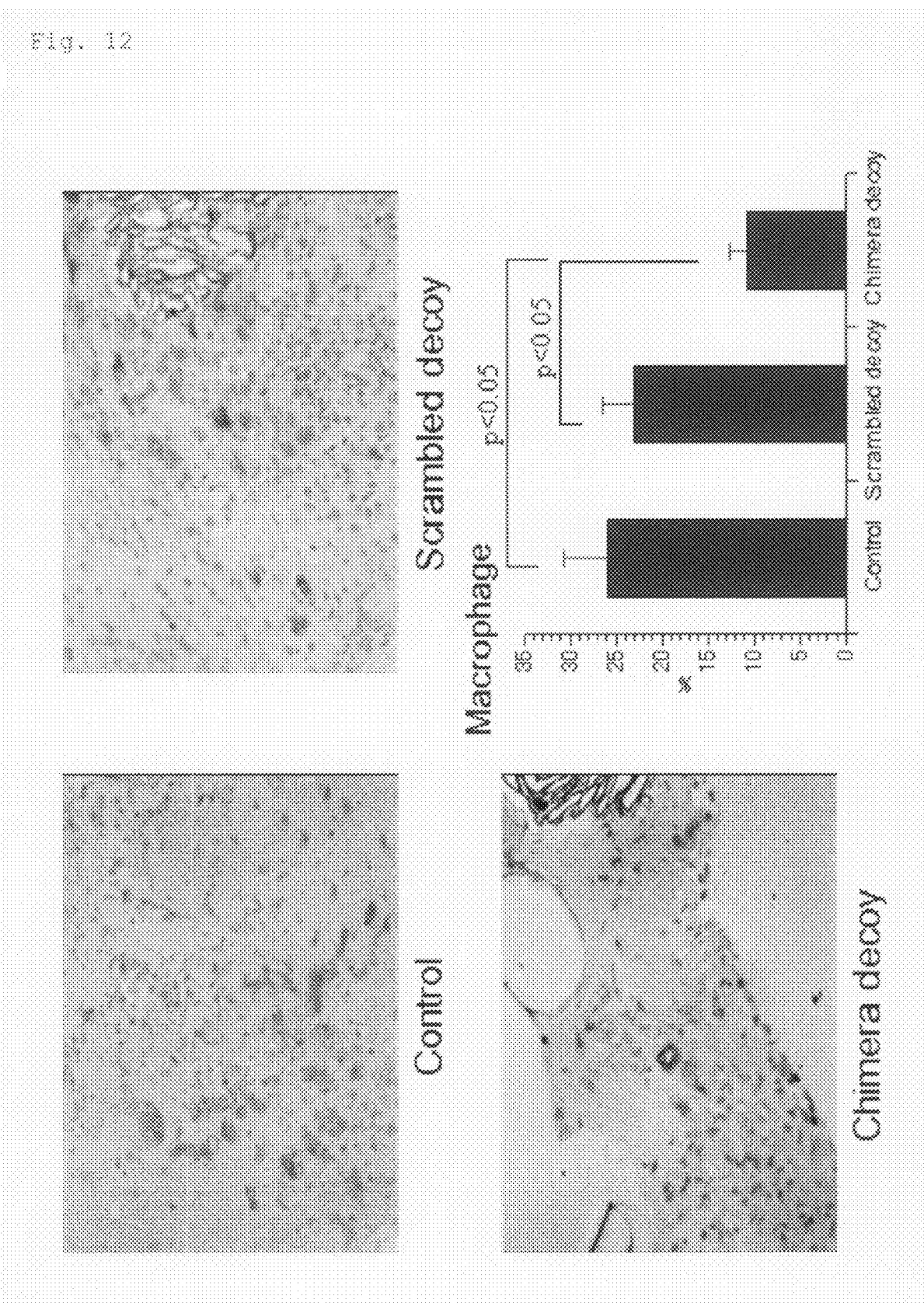
FIG. 12 shows micrographs of immunohistochemical staining of macrophages of graft anastomosed sites excised from a rabbit bypass model (magnification: ×400) and a graph showing the proportions of macrophages among all cells.

Results: The chimera decoy significantly inhibited invasion of macrophages as compared with the scrambled decoy (see Table 7, FIG. 12). In addition, since the chimera decoy decreased the number of PCNA-positive cells as compared with the scrambled decoy, the chimera decoy was indicated to inhibit cell proliferation (see Table 8, FIG. 13).

TABLE 7

| Macrophage | (% among all cells) |
|---|---|
| Control | 25.88 ± 4.71 |
| Scrambled decoy | 22.95 ± 3.51 |
| Chimera decoy | 10.69 ± 1.88 |

TABLE 8

| PCNA-positive cells | (% among all cells) |
|---|---|
| Control | 36.09 ± 6.56 |
| Scrambled decoy | 35.55 ± 6.16 |
| Chimera decoy | 12.09 ± 2.08 |

6. All Statistical Analysis Data are Shown as the Mean±Standard Error (SEM).

The invention claimed is:

1. A chimera (double) decoy consisting of SEQ ID NO:1, wherein SEQ ID NO:1 comprises an NF-κB transcriptional regulatory factor binding sequence and an E2F transcriptional regulatory factor binding sequence.

* * * * *

SEQUENCE LISTING

<160> NUMBER OF SEQ ID NOS: 20

<210> SEQ ID NO 1
<211> LENGTH: 28
<212> TYPE: DNA
<213> ORGANISM: Artificial Sequence
<220> FEATURE:
<223> OTHER INFORMATION: NF-kappaB, E2F Chimera decoy

<400> SEQUENCE: 1
gaagggattt ccctccattt cccgcgga                                          28

<210> SEQ ID NO 2
<211> LENGTH: 10
<212> TYPE: DNA
<213> ORGANISM: Artificial Sequence
<220> FEATURE:
<223> OTHER INFORMATION: NF-kappaB consensus

<400> SEQUENCE: 2 gggrhtyyhc                                                              10

<210> SEQ ID NO 3
<211> LENGTH: 8
<212> TYPE: DNA
<213> ORGANISM: Artificial Sequence
<220> FEATURE:
<223> OTHER INFORMATION: E2F consensus

<400> SEQUENCE: 3 tttsscgs                                                                 8

<210> SEQ ID NO 4
<211> LENGTH: 6
<212> TYPE: DNA
<213> ORGANISM: Artificial Sequence
<220> FEATURE:
<223> OTHER INFORMATION: GATA-3 consensus

<400> SEQUENCE: 4 wgatar                                                                   6

<210> SEQ ID NO 5
<211> LENGTH: 9
<212> TYPE: DNA
<213> ORGANISM: Artificial Sequence
<220> FEATURE:
<221> NAME/KEY:
<222> LOCATION: 4, 5, 6
<223> OTHER INFORMATION: n = a or c or g or t
<220> FEATURE:
<223> OTHER INFORMATION: STAT-1 consensus

<400> SEQUENCE: 5 ttcnnngaa                                                                9

<210> SEQ ID NO 6
<211> LENGTH: 10
<212> TYPE: DNA
<213> ORGANISM: Artificial Sequence
<220> FEATURE:
<221> NAME/KEY:
<222> LOCATION: 4, 5, 6, 7
<223> OTHER INFORMATION: n = a or c or g or t

```
<220> FEATURE:
<223> OTHER INFORMATION: STAT-6 consensus

<400> SEQUENCE: 6 ttcnnnngaa                                                              10

<210> SEQ ID NO 7
<211> LENGTH: 5
<212> TYPE: DNA
<213> ORGANISM: Artificial Sequence
<220> FEATURE:
<223> OTHER INFORMATION: Ets consensus

<400> SEQUENCE: 7 mggaw                                                                    5

<210> SEQ ID NO 8
<211> LENGTH: 7
<212> TYPE: DNA
<213> ORGANISM: Artificial Sequence
<220> FEATURE:
<223> OTHER INFORMATION: AP-1 consensus

<400> SEQUENCE: 8 tgastma                                                                  7

<210> SEQ ID NO 9
<211> LENGTH: 10
<212> TYPE: DNA
<213> ORGANISM: Artificial Sequence
<220> FEATURE:
<223> OTHER INFORMATION: NF-kappaB binding sequence

<400> SEQUENCE: 9
gggatttccc                                                              10

<210> SEQ ID NO 10
<211> LENGTH: 10
<212> TYPE: DNA
<213> ORGANISM: Artificial Sequence
<220> FEATURE:
<223> OTHER INFORMATION: NF-kappaB binding sequence

<400> SEQUENCE: 10
gggactttcc                                                              10

<210> SEQ ID NO 11
<211> LENGTH: 8
<212> TYPE: DNA
<213> ORGANISM: Artificial Sequence
<220> FEATURE:
<223> OTHER INFORMATION: E2F binding sequence

<400> SEQUENCE: 11 tttcccgc                                                                 8

<210> SEQ ID NO 12
<211> LENGTH: 6
<212> TYPE: DNA
<213> ORGANISM: Artificial Sequence
<220> FEATURE:
<223> OTHER INFORMATION: GATA-3 binding sequence

<400> SEQUENCE: 12 agatag                                                                   6
```

```
<210> SEQ ID NO 13
<211> LENGTH: 9
<212> TYPE: DNA
<213> ORGANISM: Artificial Sequence
<220> FEATURE:
<223> OTHER INFORMATION: STAT-1 binding sequence

<400> SEQUENCE: 13 ttccgggaa                                                                   9

<210> SEQ ID NO 14
<211> LENGTH: 10
<212> TYPE: DNA
<213> ORGANISM: Artificial Sequence
<220> FEATURE:
<223> OTHER INFORMATION: STAT-6 binding sequence

<400> SEQUENCE: 14
ttcccaagaa                                                                 10

<210> SEQ ID NO 15
<211> LENGTH: 5
<212> TYPE: DNA
<213> ORGANISM: Artificial Sequence
<220> FEATURE:
<223> OTHER INFORMATION: Ets binding sequence

<400> SEQUENCE: 15 cggaa                                                                       5

<210> SEQ ID NO 16
<211> LENGTH: 7
<212> TYPE: DNA
<213> ORGANISM: Artificial Sequence
<220> FEATURE:
<223> OTHER INFORMATION: AP-1binding sequence

<400> SEQUENCE: 16 tgagtca                                                                     7

<210> SEQ ID NO 17
<211> LENGTH: 28
<212> TYPE: DNA
<213> ORGANISM: Artificial Sequence
<220> FEATURE:
<223> OTHER INFORMATION: scrambled decoy

<400> SEQUENCE: 17
cgtacctgac ttagccattt cgagcgga                                             28

<210> SEQ ID NO 18
<211> LENGTH: 20
<212> TYPE: DNA
<213> ORGANISM: Artificial Sequence
<220> FEATURE:
<223> OTHER INFORMATION: NF-kappaB decoy

<400> SEQUENCE: 18
ccttgaaggg atttccctcc                                                      20

<210> SEQ ID NO 19
<211> LENGTH: 14
<212> TYPE: DNA
<213> ORGANISM: Artificial Sequence
<220> FEATURE:
<223> OTHER INFORMATION: E2F decoy

<400> SEQUENCE: 19
```

```
ctagatttcc cgcg                                               14

<210> SEQ ID NO 20
<211> LENGTH: 14
<212> TYPE: DNA
<213> ORGANISM: Artificial Sequence
<220> FEATURE:
<223> OTHER INFORMATION: E2F decoy (complementary strand of SEQ ID
      NO:19)

<400> SEQUENCE: 20
gatccgcggg aaat                                               14
```